United States Patent [19]

Block et al.

[11] Patent Number: 4,675,420

[45] Date of Patent: Jun. 23, 1987

[54] GENERATION OF REDUCED PRESSURE IN APPARATUSES IN THE PREPARATION OF PHTHALIC ANHYDRIDE AND MALEIC ANHYDRIDE

[75] Inventors: Ulrich Block, Ludwigshafen; Wolf Muff, Laumersheim; Klaus Nixdorf, Bobenheim-Roxheim; Joachim Wagner, Ludwigshafen, all of Fed. Rep. of Germany

[73] Assignee: BASF Aktiengesellschaft, Fed. Rep. of Germany

[21] Appl. No.: 775,345

[22] Filed: Sep. 11, 1985

[30] Foreign Application Priority Data

Sep. 12, 1984 [DE] Fed. Rep. of Germany ....... 3433401

[51] Int. Cl.⁴ .................. C07D 307/60; C07D 307/89
[52] U.S. Cl. ..................................... 549/248; 549/257
[58] Field of Search ............................... 549/248, 257

[56] References Cited

U.S. PATENT DOCUMENTS 4,269,776  5/1981  Keunecke et al. .................. 549/248

Primary Examiner—Richard L. Raymond
Attorney, Agent, or Firm—Keil & Weinkauf

[57] ABSTRACT

In apparatuses for the preparation of phthalic anhydride and/or maleic anhydride by catalytic oxidation of naphthalene or o-xylene with air, reduced pressure is generated using liquid-jet pumps, and wash liquid is removed from the exit gas washer as a pump fluid for the liquid-jet pumps and is subsequently recycled to the exit gas washer.

4 Claims, 1 Drawing Figure

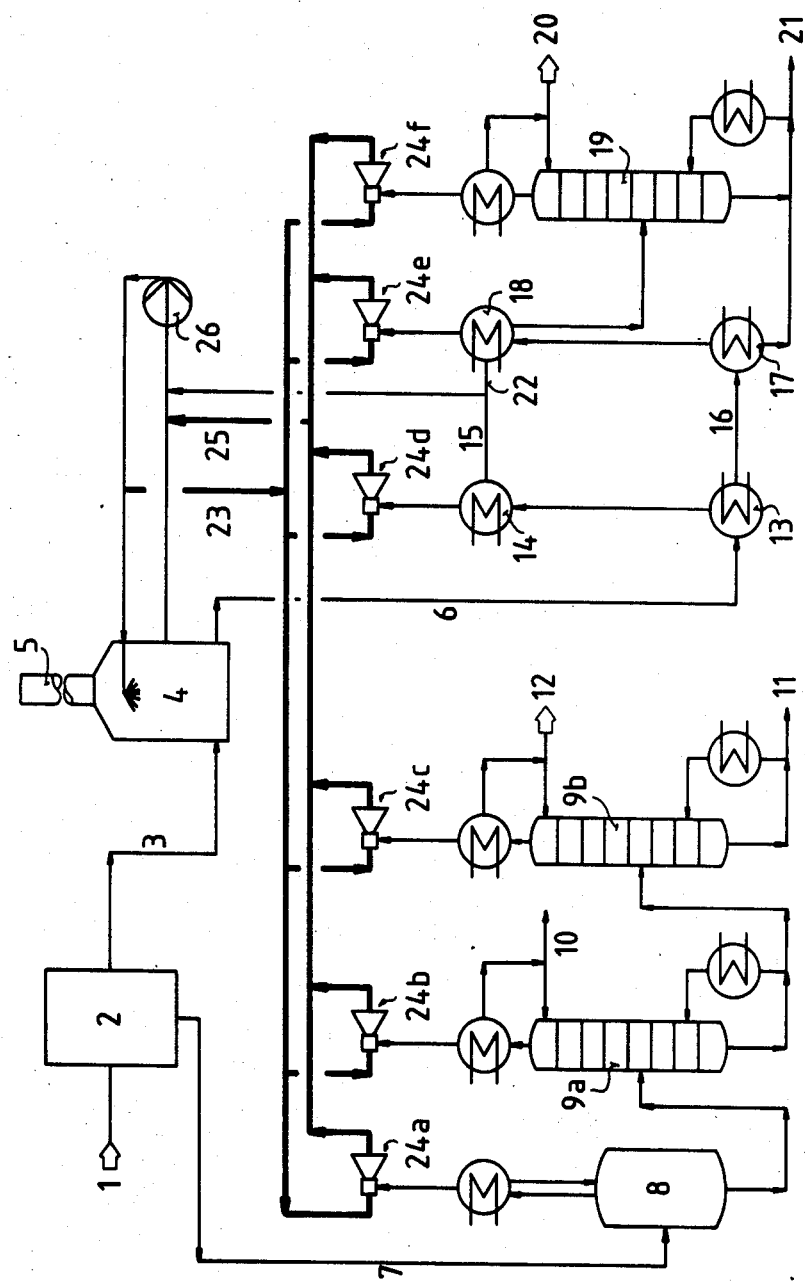

GENERATION OF REDUCED PRESSURE IN APPARATUSES IN THE PREPARATION OF PHTHALIC ANHYDRIDE AND MALEIC ANHYDRIDE

The present invention relates to a method for generating reduced pressure in apparatuses in the preparation of phthalic anhydride (PA) and/or maleic anhydride (MA) by catalytic oxidation of naphthalene or o-xylene with air.

In the process for the preparation of PA by catalytic oxidation of naphthalene or o-xylene with air, as described in the reference work Ullmanns Encyklopädie der technischen Chemie, 4th edition, volume 18, pages 526–532, PA is isolated from the exit gas from the reactor by cooling the latter in separators, while MA is removed from this gas by a downstream exit gas wash. Pure PA is obtained from the impure PA by thermal pretreatment followed by distillation. The maleic acid solution obtained after the exit gas wash is concentrated by evaporating water, the concentrated maleic acid is vaporized, and an MA which is still impure is obtained from the resulting vapor by partial condensation and then purified by distillation.

The preparation of pure PA and pure MA described above is carried out partly under reduced pressure, absolute pressures of from 1000 to 100 mbar being used. This reduced pressure is generated using water ring pumps or one-stage or two-stage steam-jet pumps.

German Patent No. 2,910,385 states that it is advantageous to use gas jet pumps for generating the reduced pressure.

The disadvantage here is that, where water ring pumps are used to generate reduced pressure, an aqueous solution is obtained which contains some of the acids filtered off under suction and has to be disposed of, and, when steam-jet pumps or gas-jet pumps are used for generating the reduced pressure, expensive pump fluids have to be used, and the resulting acid-containing pump fluids must also be disposed of. Another disadvantage is that the installation and operation of water ring pumps, steam-jet pumps and gas-jet-pumps are uneconomical.

It is an object of the present invention to reduce the cost of installation and operation of the plant components required for generating reduced pressure in apparatuses for the preparation of PA and MA. Moreover, it is intended to simplify the disposal of the pump fluid for generating reduced pressure.

We have found that this object is achieved, according to the invention, by a method in which the reduced pressure in apparatuses is generated using liquid jet pumps, wash liquid being removed from the exit gas washer as a pump fluid for the liquid jet pumps and subsequently being recycled to the exit gas washer.

The subclaims relate to further features of the method according to the invention.

The basic concept of the invention consists in the use of liquid jet pumps for generating reduced pressure in apparatuses for the preparation of PA and MA, wash liquid from the exit gas washer being used as the pump fluid. During generation of the reduced pressure, this wash liquid becomes enriched with acids and anhydrides filtered off under suction, and is then recycled to the exit gas washer.

This method avoids the necessity of disposing of the pump fluids used in the conventional methods, eg. water, steam or inert gases, which are enriched with anhydrides and acids after generation of the reduced pressure, ie. the plant components hitherto required for this purpose can be dispensed with. Another advantage is that the energy consumption for operating the liquid jet pumps is substantially smaller than for the plant components used hitherto, eg. water ring pumps, steam-jet pumps or gas-jet pumps.

An embodiment of the novel method is illustrated in the drawing and described below. The drawing shows a simplified flow chart of the process.

In the flow chart of the process, the reaction gas 1 which emerges from the reactor and is then cooled to about 180° C. is passed into the separator 2, in which impure PA is deposited in solid form. The gas stream 3 which is cooled to about 50° C. in the separator is fed to the exit gas washer 4, where the gas stream is purified by washing with water and is released into the atmosphere via the chimney 5, while the aqueous maleic acid obtained during the wash is removed from the exit gas washer as stream 6. The impure PA is melted in separator 2 and fed, as stream 7, into the pretreatment apparatus 8 and the distillation columns 9a and 9b and purified by distillation, low-boiling impurities being removed as stream 10, high-boiling residues as stream 11, and pure PA as stream 12. The aqueous maleic acid 6 is concentrated under reduced pressure in the vaporizer 13. The vaporized water is condensed in condenser 14, removed as stream 15 and fed to the exit gas washer. The concentrated maleic acid passes as stream 16 into the vaporizer 17, in which it is split up under reduced pressure into MA and water by supplying heat. MA and water are fed to the condenser 18, in which impure MA is condensed out under reduced pressure. This impure MA is then separated into pure MA as top product 20 and high-boiling residues 21 in distillation column 19 under reduced pressure. The stream taken off from the condenser 18 is fed to a further condensation unit (not shown in the drawing) operated at a lower temperature, and is condensed and then fed as stream 22 to the exit gas washer.

To generate the reduced pressure, a stream 23 is removed from the exit gas washer and is fed as a pump fluid through the liquid jet pumps 24a, b, c, d, e and f, which are connected to the appropriate plant components under reduced pressure. The stream 25, enriched with acids, is recycled to the exit gas washer by means of the pump 26.

We claim:
1. A method for the preparation of phthalic anhydride and/or maleic anhydride by catalytic oxidation of naphthalene or o-oxylene with air, wherein
   phthalic anhydride is isolated from a reaction gas by cooling in a separator and aqueous maleic acid is recovered from said reaction gas by a downstream exit gas wash;
   the isolated phthalic anhydride is fed into thermal pretreatment apparatus followed by purification in distillation apparatus;
   the aqueous maleic acid is fed into concentration, vaporization and distillation apparatus to obtain purified maleic anhydride;
   the improvement comprising generating reduce pressure in said apparatuses by recycling wash liquid from said exit gas washer through liquid jet pumps connected to said apparatuses, said wash liquid being pump fluid for said liquid jet pumps and subsequently being recycled to said exit gas washer.

2. A method as claimed in claim 1, wherein a steam-jet pump is connected between the apparatus under reduced pressure and the liquid jet pump in such a way that the steam-jet pump extracts from the apparatus and delivers into the liquid-jet pump.

3. A method as claimed in claim 1, wherein a condenser is connected between the steam-jet pump and the liquid-jet pump, by means of which condenser substantial liquefaction of the vapors released by the steam-jet pump is achieved.

4. A method as claimed in claim 1, wherein a plurality of steam-jet pumps, each having a downstream condenser, are arranged between the apparatus under reduced pressure and the liquid-jet pump.

* * * * *